(12) United States Patent
Dorn (10) Patent No.: US 11,109,990 B2
(45) Date of Patent: *Sep. 7, 2021

(54) CATHETER DELIVERY DEVICE (71) Applicant: C.R. Bard, Inc., Murray Hill, NJ (US)

(72) Inventor: Juergen Dorn, Neulussheim (DE)

(73) Assignee: C. R. Bard, Inc., Franklin Lakes, NJ (US)

( * ) Notice: Subject to any disclaimer, the term of this patent is extended or adjusted under 35 U.S.C. 154(b) by 498 days.

This patent is subject to a terminal disclaimer.

(21) Appl. No.: 15/659,496

(22) Filed: Jul. 25, 2017

(65) Prior Publication Data
US 2017/0333234 A1 Nov. 23, 2017

Related U.S. Application Data (63) Continuation of application No. 12/481,985, filed on Jun. 10, 2009, now Pat. No. 9,750,625.
(Continued)

(30) Foreign Application Priority Data

Jun. 11, 2008 (GB) ...................................... 0810749

(51) Int. Cl.
*A61F 2/95* (2013.01)
*A61F 2/962* (2013.01)
*A61M 25/00* (2006.01)

(52) U.S. Cl.
CPC ................ *A61F 2/95* (2013.01); *A61F 2/962* (2013.01); *A61M 25/0052* (2013.01)

(58) Field of Classification Search
CPC .......... A61F 2/95–97; A61F 2002/9505–9665; A61F 2/962; A61F 2/966; A61F 2/954;
(Continued)

(56) References Cited

U.S. PATENT DOCUMENTS 3,642,068 A 2/1972 Fitch et al.
4,719,853 A 1/1988 Bowers
(Continued)

FOREIGN PATENT DOCUMENTS

CA 2202870 A1 5/1996
DE 3019995 A1 12/1981
(Continued)

OTHER PUBLICATIONS

JP 2011-512895 Office Action dated Mar. 27, 2013.
(Continued)

*Primary Examiner* — Katherine H Schwiker
(74) *Attorney, Agent, or Firm* — Rutan & Tucker LLP (57) ABSTRACT A catheter delivery device for a self-expanding stent is described. The delivery device includes a distal catheter component and a distal sheath that releases the stent by moving proximally relative to the distal catheter component and the stent. A proximal catheter shaft including a tube and a pull wire within a lumen of the tube may be provided, the pull wire being attached to the distal sheath such that pulling the pull wire proximally relative to the tube pulls the distal sheath proximally to release the stent progressively. A casing tube may be provided to surround the catheter shaft, the casing tube having a distal end that receives telescopically a proximal end of the distal sheath.

15 Claims, 2 Drawing Sheets

Related U.S. Application Data (60) Provisional application No. 61/060,568, filed on Jun. 11, 2008.

(58) Field of Classification Search
CPC ........ A61F 2/958; A61F 2/2427; A61F 2/243; A61F 2/2436; A61F 2/2439; A61F 2/9517; A61F 2/9661; A61F 2/9662; A61F 2/97; A61F 2002/9517; A61F 2002/9665; A61F 2002/9511; A61F 2002/9522; A61F 2002/9528; A61F 2002/9534; A61F 2002/9583; A61F 2002/9586; A61M 25/0012–0013; A61M 25/005–0054

See application file for complete search history.

(56) References Cited

U.S. PATENT DOCUMENTS

| | | | |
|---|---|---|---|
| 5,120,323 | A | 6/1992 | Shockey et al. |
| 5,159,937 | A | 11/1992 | Tremulis |
| 5,246,008 | A | 9/1993 | Mueller |
| 5,456,665 | A | 10/1995 | Postell et al. |
| 5,474,563 | A | 12/1995 | Myler et al. |
| 5,484,425 | A | 1/1996 | Fischell et al. |
| 5,484,444 | A | 1/1996 | Braunschweiler et al. |
| 5,507,766 | A | 4/1996 | Kugo et al. |
| 5,533,987 | A | 7/1996 | Pray et al. |
| 5,573,520 | A | 11/1996 | Schwartz et al. |
| 5,591,194 | A | 1/1997 | Berthiaume |
| 5,628,754 | A | 5/1997 | Shevlin et al. |
| 5,649,908 | A | 7/1997 | Itoh |
| 5,676,659 | A * | 10/1997 | McGurk ........... A61M 25/0012 138/124 |
| 5,702,373 | A | 12/1997 | Samson |
| 5,702,418 | A | 12/1997 | Ravenscroft |
| 5,718,159 | A | 2/1998 | Thompson |
| 5,741,429 | A | 4/1998 | Donadio, III et al. |
| 5,772,669 | A * | 6/1998 | Vrba ........................... A61F 2/95 606/195 |
| 5,951,539 | A | 9/1999 | Nita et al. |
| 5,957,930 | A | 9/1999 | Vrba |
| 5,968,052 | A | 10/1999 | Sullivan, III et al. |
| 6,013,019 | A | 1/2000 | Fischell et al. |
| 6,027,863 | A | 2/2000 | Donadio, III |
| 6,042,588 | A | 3/2000 | Munsinger et al. |
| 6,053,903 | A | 4/2000 | Samson |
| 6,107,004 | A | 8/2000 | Donadio, III |
| 6,254,611 | B1 | 7/2001 | Vrba |
| 6,258,080 | B1 | 7/2001 | Samson |
| 6,296,622 | B1 | 10/2001 | Kurz et al. |
| 6,306,145 | B1 | 10/2001 | Leschinsky |
| 6,331,186 | B1 | 12/2001 | Wang et al. |
| 6,342,066 | B1 | 1/2002 | Toro et al. |
| 6,350,278 | B1 | 2/2002 | Lenker et al. |
| 6,352,553 | B1 | 3/2002 | van der Burg et al. |
| 6,352,561 | B1 | 3/2002 | Leopold et al. |
| 6,355,060 | B1 | 3/2002 | Lenker et al. |
| 6,361,555 | B1 | 3/2002 | Wilson |
| 6,368,344 | B1 * | 4/2002 | Fitz ........................... A61F 2/95 606/108 |
| 6,371,979 | B1 | 4/2002 | Beyar et al. |
| 6,375,676 | B1 | 4/2002 | Cox |
| 6,380,457 | B1 | 4/2002 | Yurek et al. |
| 6,387,118 | B1 | 5/2002 | Hanson |
| 6,391,050 | B1 | 5/2002 | Broome |
| 6,391,051 | B2 | 5/2002 | Sullivan, III et al. |
| 6,402,760 | B1 | 6/2002 | Fedida |
| 6,413,269 | B1 | 7/2002 | Bui et al. |
| 6,425,898 | B1 | 7/2002 | Wilson et al. |
| 6,432,129 | B2 | 8/2002 | DiCaprio |
| 6,443,979 | B1 | 9/2002 | Stalker et al. |
| 6,468,298 | B1 | 10/2002 | Pelton |
| 6,482,211 | B1 | 11/2002 | Choi |
| 6,482,221 | B1 | 11/2002 | Hebert et al. |
| 6,488,694 | B1 | 12/2002 | Lau et al. |
| 6,505,066 | B2 | 1/2003 | Berg et al. |
| 6,514,280 | B1 | 2/2003 | Gilson |
| 6,517,547 | B1 | 2/2003 | Feeser et al. |
| 6,517,569 | B2 | 2/2003 | Mikus et al. |
| 6,520,983 | B1 | 2/2003 | Colgan et al. |
| 6,530,947 | B1 | 3/2003 | Euteneuer et al. |
| 6,554,841 | B1 | 4/2003 | Yang |
| 6,572,643 | B1 | 6/2003 | Gharibadeh |
| 6,576,806 | B1 | 6/2003 | Slaugh et al. |
| 6,579,297 | B2 | 6/2003 | Bicek et al. |
| 6,582,460 | B1 | 6/2003 | Cryer |
| 6,592,569 | B2 | 7/2003 | Bigus et al. |
| 6,592,617 | B2 | 7/2003 | Thompson |
| 6,599,296 | B1 | 7/2003 | Gillick et al. |
| 6,599,304 | B1 | 7/2003 | Selmon et al. |
| 6,605,109 | B2 | 8/2003 | Fiedler |
| 6,607,551 | B1 | 8/2003 | Sullivan et al. |
| 6,616,996 | B1 | 9/2003 | Keith et al. |
| 6,626,934 | B2 | 9/2003 | Blaeser et al. |
| 6,629,981 | B2 | 10/2003 | Bui et al. |
| 6,629,992 | B2 | 10/2003 | Bigus et al. |
| 6,641,606 | B2 | 11/2003 | Ouriel et al. |
| 6,656,212 | B2 | 12/2003 | Ravenscroft et al. |
| 6,656,213 | B2 | 12/2003 | Solem |
| 6,660,031 | B2 | 12/2003 | Tran et al. |
| 6,663,666 | B1 | 12/2003 | Quiachon et al. |
| 6,676,666 | B2 | 1/2004 | Vrba et al. |
| 6,676,693 | B1 | 1/2004 | Belding et al. |
| 6,689,120 | B1 | 2/2004 | Gerdts |
| 6,695,862 | B2 | 2/2004 | Cox et al. |
| 6,699,274 | B2 | 3/2004 | Stinson |
| 6,702,843 | B1 | 3/2004 | Brown et al. |
| 6,726,712 | B1 | 4/2004 | Raeder-Devens et al. |
| 6,726,714 | B2 | 4/2004 | DiCaprio et al. |
| 6,736,839 | B2 | 5/2004 | Cummings |
| 6,743,219 | B1 | 6/2004 | Dwyer et al. |
| 6,749,627 | B2 | 6/2004 | Thompson et al. |
| 6,773,446 | B1 | 8/2004 | Dwyer et al. |
| 6,780,199 | B2 | 8/2004 | Solar et al. |
| 6,786,918 | B1 | 9/2004 | Krivoruchko et al. |
| 6,790,221 | B2 | 9/2004 | Monroe et al. |
| 6,827,731 | B2 | 12/2004 | Armstrong et al. |
| 6,830,575 | B2 | 12/2004 | Stenzel et al. |
| 6,843,802 | B1 | 1/2005 | Villalobos et al. |
| 6,849,084 | B2 | 2/2005 | Rabkin et al. |
| 6,858,034 | B1 | 2/2005 | Hijlkema et al. |
| 6,860,898 | B2 | 3/2005 | Stack et al. |
| 6,866,669 | B2 | 3/2005 | Buzzard et al. |
| 6,884,259 | B2 | 4/2005 | Tran et al. |
| 6,899,727 | B2 | 5/2005 | Armstrong et al. |
| 6,926,732 | B2 | 8/2005 | Derus et al. |
| 6,939,352 | B2 | 9/2005 | Buzzard et al. |
| 6,942,688 | B2 | 9/2005 | Bartholf et al. |
| 6,945,989 | B1 | 9/2005 | Betelia et al. |
| 7,001,423 | B2 | 2/2006 | Euteneuer et al. |
| 7,025,773 | B2 | 4/2006 | Gittings et al. |
| 7,052,511 | B2 | 5/2006 | Weldon et al. |
| 7,052,513 | B2 | 5/2006 | Thompson |
| 7,074,236 | B2 | 7/2006 | Rabkin et al. |
| 7,118,005 | B2 | 10/2006 | Shimazaki |
| 7,147,657 | B2 | 12/2006 | Chiang et al. |
| 7,163,552 | B2 | 1/2007 | Diaz |
| 7,172,617 | B2 | 2/2007 | Colgan et al. |
| 7,172,618 | B2 | 2/2007 | Lupton |
| 7,198,636 | B2 | 4/2007 | Cully et al. |
| 7,297,302 | B2 | 11/2007 | Berg et al. |
| 7,303,580 | B2 | 12/2007 | Parker |
| 7,320,702 | B2 | 1/2008 | Hammersmark et al. |
| 7,387,640 | B2 | 6/2008 | Cummings |
| 7,454,422 | B2 | 11/2008 | Chan et al. |
| 7,455,688 | B2 | 11/2008 | Furst et al. |
| 7,462,192 | B2 | 12/2008 | Norton et al. |
| 7,468,070 | B2 | 12/2008 | Henry et al. |
| 7,517,361 | B1 | 4/2009 | Ravenscroft |
| 7,550,001 | B2 | 6/2009 | Dorn et al. |
| 7,553,322 | B2 | 6/2009 | Dorn et al. |
| 7,717,949 | B2 | 5/2010 | Dorn |
| 7,758,624 | B2 | 7/2010 | Dorn et al. |

(56) References Cited

U.S. PATENT DOCUMENTS

| | | |
|---|---|---|
| 7,867,267 B2 | 1/2011 | Sullivan et al. |
| 8,075,606 B2 | 12/2011 | Dorn |
| 8,206,348 B2 | 6/2012 | McDermott et al. |
| 8,652,193 B2 | 2/2014 | Dorn |
| 9,750,625 B2 | 9/2017 | Dorn |
| 2001/0034549 A1 | 10/2001 | Bartholf et al. |
| 2001/0049547 A1 | 12/2001 | Moore |
| 2001/0056299 A1 | 12/2001 | Thompson |
| 2002/0016597 A1 | 2/2002 | Dwyer et al. |
| 2002/0028984 A1 | 3/2002 | Hayakawa et al. |
| 2002/0077691 A1 | 6/2002 | Nachtigall |
| 2002/0128678 A1* | 9/2002 | Petersen ............... A61F 2/95 606/200 |
| 2002/0133127 A1 | 9/2002 | Collins |
| 2002/0133141 A1 | 9/2002 | Sparks et al. |
| 2003/0050686 A1 | 3/2003 | Raeder-Devens et al. |
| 2003/0055447 A1 | 3/2003 | Lee et al. |
| 2003/0093106 A1 | 5/2003 | Brady et al. |
| 2003/0114911 A1 | 6/2003 | Lupton |
| 2004/0006380 A1 | 1/2004 | Buck et al. |
| 2004/0073293 A1 | 4/2004 | Thompson |
| 2004/0087933 A1 | 5/2004 | Lee et al. |
| 2004/0106977 A1 | 6/2004 | Sullivan et al. |
| 2004/0127912 A1 | 7/2004 | Rabkin et al. |
| 2004/0148009 A1 | 7/2004 | Buzzard et al. |
| 2004/0153049 A1 | 8/2004 | Hewitt et al. |
| 2004/0153137 A1 | 8/2004 | Gaschino et al. |
| 2004/0193180 A1 | 9/2004 | Buzzard et al. |
| 2004/0215229 A1 | 10/2004 | Coyle |
| 2004/0215317 A1 | 10/2004 | Cummings |
| 2004/0230286 A1 | 11/2004 | Moore et al. |
| 2004/0267281 A1 | 12/2004 | Harari et al. |
| 2005/0004515 A1 | 1/2005 | Hart et al. |
| 2005/0004553 A1* | 1/2005 | Douk ............... A61B 17/12022 604/523 |
| 2005/0021123 A1 | 1/2005 | Dorn et al. |
| 2005/0027345 A1 | 2/2005 | Horan et al. |
| 2005/0033403 A1 | 2/2005 | Ward et al. |
| 2005/0065590 A1 | 3/2005 | Shelso |
| 2005/0065591 A1 | 3/2005 | Moberg et al. |
| 2005/0080476 A1 | 4/2005 | Gunderson et al. |
| 2005/0090887 A1 | 4/2005 | Pryor |
| 2005/0090890 A1 | 4/2005 | Wu et al. |
| 2005/0165352 A1 | 7/2005 | Henry et al. |
| 2005/0182475 A1 | 8/2005 | Jen et al. |
| 2005/0209671 A1 | 9/2005 | Ton et al. |
| 2005/0209675 A1 | 9/2005 | Ton et al. |
| 2005/0246008 A1 | 11/2005 | Hogendijk et al. |
| 2005/0246010 A1 | 11/2005 | Alexander et al. |
| 2005/0288762 A1 | 12/2005 | Henderson et al. |
| 2006/0004438 A1 | 1/2006 | Alexander et al. |
| 2006/0015168 A1 | 1/2006 | Gunderson |
| 2006/0020321 A1 | 1/2006 | Parker |
| 2006/0030923 A1 | 2/2006 | Gunderson |
| 2006/0041302 A1 | 2/2006 | Malewicz |
| 2006/0058865 A1 | 3/2006 | Case et al. |
| 2006/0074409 A1 | 4/2006 | Schuermann |
| 2006/0074478 A1 | 4/2006 | Feller |
| 2006/0089627 A1 | 4/2006 | Burnett et al. |
| 2006/0095110 A1 | 5/2006 | Moberg et al. |
| 2006/0100687 A1 | 5/2006 | Fahey et al. |
| 2006/0100688 A1 | 5/2006 | Jordan et al. |
| 2006/0106455 A1 | 5/2006 | Furst et al. |
| 2006/0111769 A1 | 5/2006 | Murray |
| 2006/0116752 A1 | 6/2006 | Norton et al. |
| 2006/0184225 A1 | 8/2006 | Pryor |
| 2006/0184227 A1 | 8/2006 | Rust |
| 2006/0190069 A1 | 8/2006 | Baker-Janis et al. |
| 2006/0200221 A1 | 9/2006 | Malewicz |
| 2006/0206189 A1 | 9/2006 | Furst et al. |
| 2006/0224112 A1 | 10/2006 | Lentz |
| 2006/0229697 A1 | 10/2006 | Gerdts et al. |
| 2006/0235502 A1 | 10/2006 | Belluche et al. |
| 2006/0247661 A1* | 11/2006 | Richards ............... A61F 2/95 606/108 |
| 2006/0253184 A1 | 11/2006 | Amplatz |
| 2006/0259118 A1 | 11/2006 | Pal et al. |
| 2006/0259123 A1 | 11/2006 | Dorn |
| 2006/0259124 A1 | 11/2006 | Matsuoka et al. |
| 2006/0271150 A1 | 11/2006 | Andreas et al. |
| 2006/0271151 A1 | 11/2006 | McGarry et al. |
| 2006/0282147 A1 | 12/2006 | Andreas |
| 2006/0282148 A1 | 12/2006 | Hammersmark et al. |
| 2006/0282149 A1 | 12/2006 | Kao |
| 2006/0282152 A1 | 12/2006 | Beyerlein et al. |
| 2006/0282157 A1 | 12/2006 | Hill et al. |
| 2007/0027521 A1 | 2/2007 | Andreas et al. |
| 2007/0027522 A1 | 2/2007 | Chang et al. |
| 2007/0043420 A1 | 2/2007 | Lostetter |
| 2007/0043421 A1 | 2/2007 | Mangiardi et al. |
| 2007/0043726 A1 | 2/2007 | Chan et al. |
| 2007/0043728 A1 | 2/2007 | Chan et al. |
| 2007/0055339 A1 | 3/2007 | George et al. |
| 2007/0055340 A1 | 3/2007 | Pryor |
| 2007/0060910 A1 | 3/2007 | Grandt et al. |
| 2007/0073373 A1 | 3/2007 | Bonsignore |
| 2007/0073379 A1 | 3/2007 | Chang |
| 2007/0073391 A1 | 3/2007 | Bourang et al. |
| 2007/0100412 A1 | 5/2007 | Dwyer et al. |
| 2007/0100413 A1 | 5/2007 | Dwyer et al. |
| 2007/0100421 A1 | 5/2007 | Griffin |
| 2007/0100422 A1 | 5/2007 | Shumer et al. |
| 2007/0106364 A1 | 5/2007 | Buzzard et al. |
| 2007/0118201 A1 | 5/2007 | Pappas et al. |
| 2007/0118207 A1 | 5/2007 | Amplatz et al. |
| 2007/0123971 A1 | 5/2007 | Kennedy et al. |
| 2007/0142892 A1 | 6/2007 | Dave et al. |
| 2007/0168014 A1 | 7/2007 | Jimenez et al. |
| 2007/0179519 A1 | 8/2007 | Huisun |
| 2007/0191864 A1 | 8/2007 | Shumer |
| 2007/0191865 A1 | 8/2007 | Pappas |
| 2007/0198048 A1 | 8/2007 | Behan et al. |
| 2007/0198050 A1 | 8/2007 | Ravenscroft et al. |
| 2007/0198076 A1 | 8/2007 | Hebert et al. |
| 2007/0199360 A1 | 8/2007 | Sarac et al. |
| 2007/0203563 A1 | 8/2007 | Hebert et al. |
| 2007/0208407 A1 | 9/2007 | Gerdts et al. |
| 2007/0213813 A1 | 9/2007 | Von Segesser et al. |
| 2007/0219612 A1 | 9/2007 | Andreas et al. |
| 2007/0219613 A1 | 9/2007 | Kao et al. |
| 2007/0219617 A1 | 9/2007 | Saint |
| 2007/0233224 A1 | 10/2007 | Leynov et al. |
| 2007/0244540 A1 | 10/2007 | Pryor |
| 2007/0250149 A1 | 10/2007 | Von Oepen et al. |
| 2007/0250151 A1 | 10/2007 | Pereira |
| 2007/0255390 A1 | 11/2007 | Ducke et al. |
| 2007/0260301 A1 | 11/2007 | Chuter et al. |
| 2007/0265694 A1 | 11/2007 | Sarac et al. |
| 2007/0270779 A1 | 11/2007 | Jacobs et al. |
| 2007/0270932 A1 | 11/2007 | Headley et al. |
| 2007/0270937 A1 | 11/2007 | Leanna |
| 2007/0293930 A1 | 12/2007 | Wang et al. |
| 2008/0009934 A1 | 1/2008 | Schneider et al. |
| 2008/0033570 A1 | 2/2008 | Blitz et al. |
| 2008/0058722 A1 | 3/2008 | Von Oepen et al. |
| 2008/0065014 A1 | 3/2008 | Von Oepen et al. |
| 2008/0071345 A1 | 3/2008 | Hammersmark et al. |
| 2008/0077223 A1 | 3/2008 | Fischell et al. |
| 2008/0103581 A1 | 5/2008 | Goto |
| 2008/0114435 A1 | 5/2008 | Bowe |
| 2008/0114442 A1 | 5/2008 | Mitchell et al. |
| 2008/0183272 A1 | 7/2008 | Wood et al. |
| 2008/0208310 A1 | 8/2008 | McDermott et al. |
| 2008/0234796 A1 | 9/2008 | Dorn |
| 2008/0255651 A1 | 10/2008 | Dwork |
| 2008/0262590 A1 | 10/2008 | Murray |
| 2008/0275541 A1 | 11/2008 | Furst et al. |
| 2008/0288043 A1 | 11/2008 | Kaufmann et al. |
| 2008/0319524 A1 | 12/2008 | Yachia et al. |
| 2009/0036967 A1 | 2/2009 | Cummings |
| 2009/0054972 A1 | 2/2009 | Norton et al. |

(56) References Cited

U.S. PATENT DOCUMENTS

| | | | |
|---|---|---|---|
| 2009/0105802 A1 | 4/2009 | Henry et al. | |
| 2009/0156998 A1* | 6/2009 | Arana | A61M 25/0054<br>604/103 |

FOREIGN PATENT DOCUMENTS

| | | | |
|---|---|---|---|
| DE | 3910157 A1 | 10/1989 |
| EP | 0303487 A2 | 2/1989 |
| EP | 0437795 A1 | 7/1991 |
| EP | 0473045 A1 | 3/1992 |
| EP | 0517075 A1 | 12/1992 |
| EP | 0608853 A2 | 8/1994 |
| EP | 0680351 A1 | 11/1995 |
| EP | 0688576 A1 | 12/1995 |
| EP | 0792656 A1 | 9/1997 |
| EP | 0807444 A2 | 11/1997 |
| EP | 0810003 A2 | 12/1997 |
| EP | 0823262 A2 | 2/1998 |
| EP | 0904795 A1 | 3/1999 |
| EP | 1364611 A1 | 11/2003 |
| EP | 1457215 A1 | 9/2004 |
| EP | 1656963 A1 | 5/2006 |
| EP | 1709987 A1 | 10/2006 |
| EP | 1747793 A1 | 1/2007 |
| EP | 1834610 A1 | 9/2007 |
| EP | 1852138 A1 | 11/2007 |
| JP | 2006-271565 A | 10/2006 |
| JP | 2007-175440 A | 7/2007 |
| JP | 2008-104657 A | 5/2008 |
| WO | 1993015785 A1 | 8/1993 |
| WO | 1996013228 A1 | 5/1996 |
| WO | 1996036298 A1 | 11/1996 |
| WO | 1997043949 A1 | 11/1997 |
| WO | 1998012988 A1 | 4/1998 |
| WO | 1999015219 A1 | 4/1999 |
| WO | 1999044541 A1 | 9/1999 |
| WO | 1999064098 A1 | 12/1999 |
| WO | 2000012031 A1 | 3/2000 |
| WO | 2001078627 A1 | 10/2001 |
| WO | 2001087180 A2 | 11/2001 |
| WO | 2005053574 A2 | 6/2005 |
| WO | 2005072391 A2 | 8/2005 |
| WO | 2006034008 A2 | 3/2006 |
| WO | 2006127931 A2 | 11/2006 |
| WO | 2006133958 A1 | 12/2006 |
| WO | 2006133959 A1 | 12/2006 |
| WO | 2006133960 A1 | 12/2006 |
| WO | 2007004221 A1 | 1/2007 |
| WO | 2007065420 A1 | 6/2007 |
| WO | 2007076114 A2 | 7/2007 |
| WO | 2007138608 A1 | 12/2007 |
| WO | 2008005666 A1 | 1/2008 |
| WO | 2008036156 A1 | 3/2008 |
| WO | 2008093851 A1 | 8/2008 |

OTHER PUBLICATIONS

JP 2011-512895 Office Action dated Mar. 28, 2014.
JP 2011-512895 Office Action dated Oct. 10, 2014.
PCT/EP2009/004199 filed Jun. 10, 2009 International Preliminary Report on Patentability dated Nov. 5, 2010.
PCT/EP2009/004199 filed Jun. 10, 2009 Search Report dated Oct. 19, 2009.
PCT/EP2009/004199 filed Jun. 10, 2009 Written Opinion dated Oct. 19, 2009.
U.S. Appl. No. 12/481,985, filed Jun. 10, 2009 Advisory Action dated May 21, 2014.
U.S. Appl. No. 12/481,985, filed Jun. 10, 2009 Advisory Action dated Oct. 22, 2012.
U.S. Appl. No. 12/481,985, filed Jun. 10, 2009 Final Office Action dated Feb. 27, 2014.
U.S. Appl. No. 12/481,985, filed Jun. 10, 2009 Final Office Action dated Jun. 29, 2012.
U.S. Appl. No. 12/481,985, filed Jun. 10, 2009 Final Office Action dated Mar. 12, 2015.
U.S. Appl. No. 12/481,985, filed Jun. 10, 2009 Non-Final Office Action dated Aug. 15, 2013.
U.S. Appl. No. 12/481,985, filed Jun. 10, 2009 Non-Final Office Action dated Dec. 22, 2011.
U.S. Appl. No. 12/481,985, filed Jun. 10, 2009 Non-Final Office Action dated Oct. 2, 2014.

* cited by examiner

CATHETER DELIVERY DEVICE

PRIORITY

This application is a continuation of U.S. patent application Ser. No. 12/481,985, filed Jun. 10, 2009, now U.S. Pat. No. 9,750,625, which claims priority to U.S. Provisional Application No. 61/060,568, filed Jun. 11, 2008, and to United Kingdom Patent Application No. 0810749.2, filed Jun. 11, 2008, each of which is incorporated by reference in its entirety into this application.

TECHNICAL FIELD

This invention relates to a catheter which is a delivery device for a self-expanding stent to be delivered to a stenting location in the body trans-luminally. The device is of the "pull wire" type and is designed for delivery of covered stents of significant length, that represent a tougher delivery task than a short bare stent. The device described below is of the "over the wire" category. However, the present invention can also be applied to "rapid exchange" catheter delivery devices. Guidewire diameters of 18 or 35 "thou" are conventional, and contemplated for use with this invention. Covered stents with deployed diameters in a range of from 6 mm to 18 mm are contemplated.

BACKGROUND

The present applicant has progressively developed delivery devices for covered stents. One example is to be found in WO 2005/053574, which is incorporated by reference in its entirety into this application. The present invention carries such architecture forward into the technical field of covered stents that are lengthier (maybe up to 120 mm, or even beyond) and so put greater demands on the strength of the delivery system during deployment of the stent, when a sheath surrounding the stent has to be pulled proximally, relative to the stent, to release the stent into the bodily lumen to be stented, progressively, starting at the distal end of covered stent. Readers will appreciate that it is characteristic of such catheter delivery devices that one of two end-to-end components is in endwise tension (the components responsible for pulling the sheath proximally) while the other of the two end-to-end components (the one that prevents the stent from being drawn proximally with the proximally moving sheath) is in end-to-end compression during progressive deployment of the stent. In general, designers of catheter delivery devices for self-expanding stents try to keep the passing diameter of the catheter to a minimum, which self-evidently conflicts with the design imperative that the end-to-end component in compression does not buckle or concertina, or otherwise lose its length integrity, during stent deployment. The present invention sacrifices ultimate narrowness of passing diameter to the objective of enhanced performance in delivering relatively lengthy covered stents, for which endwise stresses in the catheter delivery device, during deployment of the stent, are likely to be higher than for shorter stents that are bare rather than covered.

Catheter delivery devices that exhibit a "pull wire" are attractive for tasks where the end-to-end stresses are relatively large, because a wire is well able to sustain endwise tension, but not so well adapted to sustain an endwise compressive stress. Better for that task is a tube. Thus, in a coaxial system, one with the tube carrying the compressive stress, and the wire within it carrying the tensile stress, will likely perform better than a system arranged the other way around. However, at the distal end of the system, where the stent is located, it is the outside sheath that is in tension, and the inside catheter element, that stops the stent moving proximally, that is in compression. Thus, somewhere between the proximal and distal end of the catheter delivery system of a pull wire architecture, there needs to be an inversion, to transfer the tensile stress from the radially inner pull wire to the radially outer sheath surrounding the stent. Clearly, any length interval between the transfer zone and the distal end of the stent, in which a relatively small diameter component of the catheter system is required to carry the endwise compressive stress during stent deployment, needs to be strong enough to retain its lengthwise integrity during such stent deployment. Self-evidently, the length of that portion should be reduced, to the extent possible.

A further problem with transfer zones in pull wire systems is to minimize any propensity for the catheter system to buckle at any particular point along its length. Evidently, there is a challenge to incorporate a transfer zone somewhere along the length of the catheter shaft, while at the same time avoiding any points long the length of the catheter where there is an increased risk of buckling.

SUMMARY

Catheter delivery devices in accordance with the present invention can feature novelty in the architecture of the part of the system that withdraws proximally to release the stent. Alternatively, they can exhibit novelty in that part of the system that retains the stent against proximal withdrawal during stent deployment. Preferably the novelty is in both of these component parts of the system, working synergistically together. Each of the contributions to the architecture of the catheter delivery device constitutes an invention in its own right, but the combination of the improved architecture pull back component, with the improved architecture of the component that carries the end-to-end compression during stent deployment, can yield synergistic results that allow the deployment through narrow tortuous lumens, of remarkably lengthy covered stent prostheses.

According to a first aspect of the present invention there is provided a catheter delivery device in which a casing tube surrounds the catheter shaft and has a distal end that receives telescopically a proximal end of the distal sheath of the device, with a pull wire fixed to a proximal end zone of the distal sheath within the lumen of the casing tube.

Normally, the casing tube proximal end is fixed to a hub of an actuating device (otherwise called "hand unit"). Conveniently, the delivery device includes a retaining ring that retains the pull wire on the radially outside surface of a proximal end zone of the distal sheath, the ring embracing the radially outside surface of the distal sheath, near its proximal end. Usefully, the distal end zone of the pull wire is thinned and given the shape of part of a cylindrical surface with a radius that corresponds to that of the radially outer cylindrical surface of the distal sheath near its proximal end, whereby the thinned end zone of the pull wire can lie flush, or close to flush, with a radially outside surface of the distal sheath and, conveniently, clamped to that outside surface by the retaining ring, which is conveniently a swaged ring.

Readers skilled in the art will be able to envisage other ways of extending a sheath into a pull wire. For example, the material of the sheath could itself be continued proximally, to form the pull wire.

In one preferred embodiment, the distal sheath exhibits a diving tube proximal of the location of the stent. The inventor calls this component of the device a "diving" tube because it "dives" into the open distal end of the casing tube and slides proximally within the lumen of the casing tube, during deployment of the stent. The diving tube has an outside diameter slightly smaller than that of more distal portions of the distal portion of the distal sheath, that embrace the stent. Conveniently, the distal end of the diving tube is fixedly received inside the open proximal end of a distal portion of the distal sheath. At the distal end of the distal portion of the distal sheath an inwardly tapered atraumatic tip can be provided, for the catheter device as a whole. Normally, the pull wire will be attached to a zone of the diving tube relatively close to the proximal end of the diving tube, inside the lumen of the casing tube.

Conventionally, in stent delivery systems, an atraumatic tip is provided on an axial component that extends through the lumen of the stent, with the stent sheath terminating proximally of that atraumatic tip. Such arrangements are compatible with the present invention and can provide embodiments of it.

In another aspect of the present invention, the inner catheter component of the delivery device includes a proximal sheath that has a lumen that contains the catheter shaft of the delivery device. It has an open distal end that receives a proximal end of the distal catheter component, side-by-side with the distal end of the catheter shaft. The proximal sheath and the distal catheter component together provide a guidewire lumen that runs the full length of the delivery device, thereby to render the delivery system a member of the "over the wire" type. In one preferred embodiment, the distal end of the catheter tube carries, to one side of the tube axis, a transfer ring that embraces the proximal end of the distal catheter component. We call this ring a "transfer" ring because it marks the transfer of endwise compressive stress during deployment of the stent, between the outer coaxial component constituted by the catheter shaft tube, and the inner coaxial component at the distal end of the delivery device, inside the distal sheath that is pulled proximally to release the stent.

Readers will be able to envisage alternatives to a transfer ring. Depending on the materials of construction of the catheter tube and the distal catheter component, these two components could be joined, side by side, with techniques such as gluing, fusion welding, strapping together or brazing, as well as form-fitting and other ways of achieving a mechanical interference that resists axial shortening.

As mentioned above, the catheter system as a whole must resist any tendency to kink under endwise compression. Transition zones are particularly vulnerable to unwanted kinking. It may therefore be worthwhile to install at the side by side component transfer zone an extra splint or sleeve, to enhance resistance to kinking in this zone.

The conventional way to stop a stent from moving proximally during proximal withdrawal of the surrounding sheath in deployment of the stent, is to provide a form of "stop ring" that the proximal end of the stent butts up against, whenever the stent seeks to move proximally. Normally, such an arrangement imposes no undue compressive stresses on any part of the stent matrix. However, in a case where the stent might be vulnerable to excessive end-to-end compressive stress, a better arrangement is to give the stent cylinder a measure of support, against proximal movement, over a greater part of the length of the stent than just the proximal end surface of the stent cylinder. Since the catheter delivery device of the present invention is specifically adapted for use with lengthy covered stents, it is advantageous to continue the distal catheter component into a stent support tube that is located, in use, inside the lumen of the stent, and supports the stent around that lumen, against proximal withdrawal relative to the distal catheter component, during proximal withdrawal of the surrounding sheath. In one preferred embodiment, the stent support tube is provided with a plurality of annular cushions that mechanically interfere with the covered luminal surface of the stent radially outside the stent support tube.

The word "cushion" is to be interpreted liberally. For example, a simple spiral protruding radially, to press against the luminal surface of the prosthesis or implant, covered stent or bare stent, can serve the desired purpose. Other arrangements are already within the published patent literature, and becoming more numerous as stent lengths continue to increase. For example, the present applicant has described various arrangements in U.S. Pat. No. 8,287,582 and U.S. Pat. No. 7,717,949, each of which is incorporated by reference in its entirety into this application.

Applicant has previously developed delivery systems for self-expanding stents in which the distal sheath and stent are free to rotate coaxially, relative to the catheter shaft. While this is still possible to engineer, with the present invention, it is envisaged also to have the stent support tube fixed to the catheter shaft without freedom to rotate thereby fixing (via the stent) the outer sheath against rotation relative to the catheter shaft. With such rotation inhibited, there is no risk that the pull wire can wrap itself around the other catheter shaft component.

The distal catheter component, where it lies proximal of the proximal end of the stent, needs to have enough column strength to resist the compressive stress imposed on it when the stent is being released. A known way to improve the column strength of a catheter component is to wrap it with a helical wire. Accordingly, in one preferred embodiment of the present invention a compound catheter portion of the distal catheter component includes a helix of wire to stiffen the compound catheter portion when the compound catheter portion is in end-to-end compression.

Readers will be well aware of the importance of achieving a high enough resistance to compressive stress, and adequate column strength. Also in this area of design, the patent literature offers the reader a range of alternatives to a helical wire wrapping. Specifically, a tube of metal, for example stainless steel or PHYNOX with a multitude of through wall slits transverse to its length direction, can combine high flexibility with high column strength. For a relevant disclosure, see WO 20061133960 and EP-A-1656963, each of which is incorporated by reference in its entirety into this application.

In one embodiment (not shown) the proximal end zone of the distal catheter component comprises a length portion that exhibits a multitude of slits with their length direction transverse to the length of the distal catheter component. Such slits can increase the flexibility in bending of the distal catheter component, at least in its proximal end zone. Usefully, the slitted length portion is extended distally towards the location of the proximal end of the stent. The distal extension would normally be all the way to the proximal end of the stent but might be less than all the way, for example, if the distal catheter component exhibits a change of material, from metal to polymer, in a zone located proximally of the proximal end of the stent.

Conveniently, the delivery device includes a connection tube with a lumen that receives, in its distal end, the proximal end of the stent support tube and, in its proximal open end, the distal end of the compound catheter portion. Adhesive compositions can be used to build the combination of the distal catheter component. The annular cushions on the stent support tube can have other forms, indeed, any suitable form of "embossing" that is capable of resisting relative axial movement of the stent, proximally, relative to the distal catheter component.

It is suggested above that cushions within the lumen of the stent can take over completely from a "pusher" ring that abuts the proximal end of the stent. Nevertheless, a ring to abut the proximal end of the stent can also be provided here. In one embodiment, it assists the cushions. In another embodiment it is deliberately spaced away from the proximal end of the prosthesis, and abuts that proximal end only in the event that the cushions somehow fail to prevent all proximal movement of the prosthesis during its deployment.

BRIEF DESCRIPTION OF THE DRAWINGS

For a better understanding of the present invention, and to show more clearly how the same may carried into effect, reference will now be made, by way of example, to the accompanying drawings, in which.

DETAILED DESCRIPTION

Figure 1:
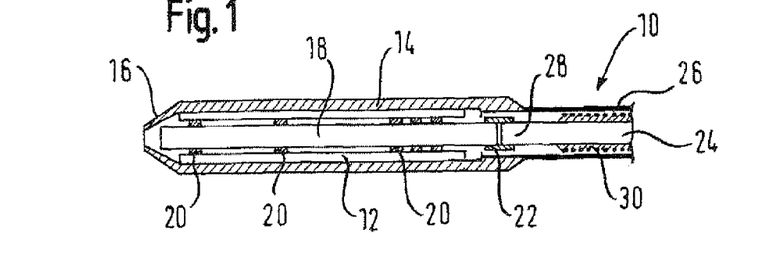
FIG. 1 is a lengthwise diametral section of a distal end portion of a first embodiment of catheter delivery device in accordance with the present invention.

The illustrated delivery system 10 is for delivering a covered stent 12 that can be seen in FIG. 1 compressed inside a distal sheath 14 that has an atraumatic tapered distal tip 16. The stent being a self-expanding stent, it is pressing on the radially inner cylindrical surface of the outer sheath 14. Inside the radially compressed stent 12 is a stent support tube 18 that defines a guidewire lumen (not visible in FIG. 1) and carries on its outer cylindrical surface a plurality of annular cushions 20. For covered stents with a length of more than 100 mm we propose three such cushions near the proximal end of the stent, one at the distal end of the stent, and one partway along the length of the stent. For shorter stents, the cushion part-way along the stent is likely not needed. The cushions are made of DYMAX material and each can be of a length along the axis of the stent that is in the area of 2 mm to 4 mm. Depending how the cushions are attached to the support tube 18, it may be beneficial to provide at the distal end of the tube a safety element, namely some form of a stopper that will stop any annular cushion inadvertently sliding off the distal end of the support tube during deployment of the stent.

In FIG. 1, the stent support tube 18 has a proximal end that is received within a short connection tube 22, that also receives the distal end of a compound catheter portion 24 based on a tube of polyamide with braid reinforcement within its annular wall thickness, that is destined to carry a lengthwise compression stress when the distal sheath 14 is pulled proximally away from the stent 12 to release it from the delivery system. What pulls the distal sheath 14 from around the sheath is a proximal portion of the distal sheath which we call a "diving sheath" 26 that has an outside diameter marginally smaller than the inside diameter of the distal sheath 14 and a distal end that is received inside the lumen at the proximal end of the distal sheath 14, where it is fixed by an adhesive composition. The diving sheath 26 surrounds the compound catheter component, with clearance. We propose that it be of braided polyamide with a wall thickness of 100 μm. In the case of relatively large diameter prosthesis, deliverable with a relatively small diameter catheter shaft, it may be that the inside diameter of the distal sheath 14 is significantly bigger than the outside diameter of the distal end of the driving sheath. In such a case it may be useful to provide an intermediate spacer sleeve between the two components.

The compound catheter component in the lumen of the diving sheath has a polyimide shaft element 28 that defines a guidewire lumen and carries glued on its outer cylindrical surface a helical wind of fine wire 30 which serves to stiffen the tube 28 against bending, without too much loss of bending flexibility, especially when the tube 28 is under endwise compression.

Before leaving FIG. 1, we draw it to the attention of readers that the distal sheath 14, without the diving sheath 26, can serve as a pre-assembly during manufacture of the catheter delivery device, with the stent support tube 18 and stent 12 being inserted into the sheath 14 to constitute the sub-assembly. At a later stage in manufacture, the tube 28 of the compound catheter portion can be connected to the stent support tube 18, for example, by heat-shrinking the polyamide connection tube 22 around both the tube 28 and the stent support tube 18, using a PET shrink tube at around 200° C. After such shrinking, the PET tube is removed and discarded. Thereafter, the diving sheath 26 can be introduced into the distal sheath 14 with or without an intervening spacer sleeve, and fixed to it with adhesive.

Figure 2:
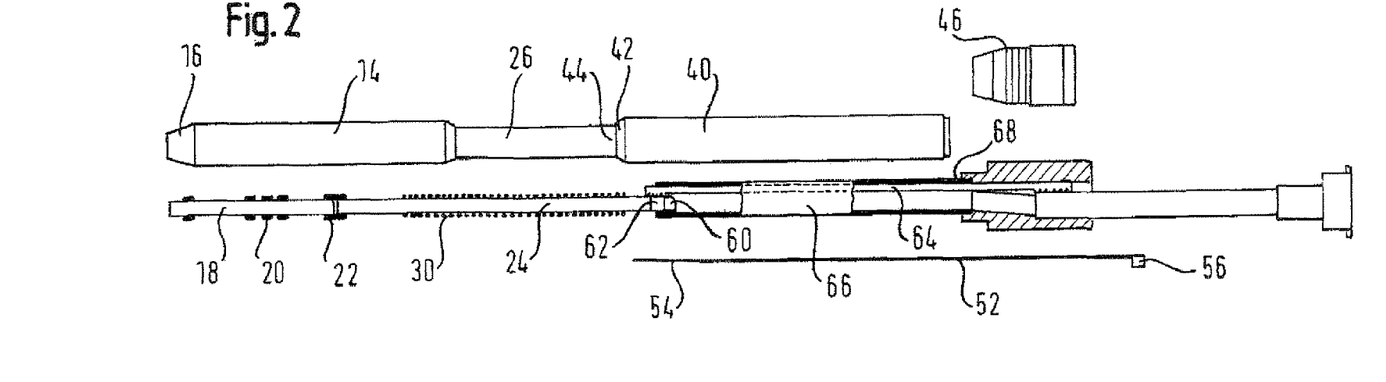
FIG. 2 is a schematic lengthwise diametral section of the delivery device of FIG. 1, partly exploded to show individual components separately.

Turning now to FIG. 2 of the drawings, we see components of the delivery device arranged in an "exploded" form, just enough to separate the components of the inner and outer coaxial members. Thus, the sub-assembly of distal sheath 14 and diving sheath 26 is shown displaced sideways from the stent support tube but coaxial with a casing tube 40 that has a distal end 42 that receives a proximal end 44 of the diving sheath 26. The proximal end of the casing tube 40 is fixed by adhesive to a strain-relieving hub 46 of a hand unit that will actuate the deployment of the stent from the delivery device. During deployment of the stent, the distal sheath 14 and diving sheath 26 move proximally, but the casing tube 40 does not, so that the proximal end of the diving sheath 26 slides proximally down the lumen of the casing tube 40, from the open distal end 42.

Figure 3:
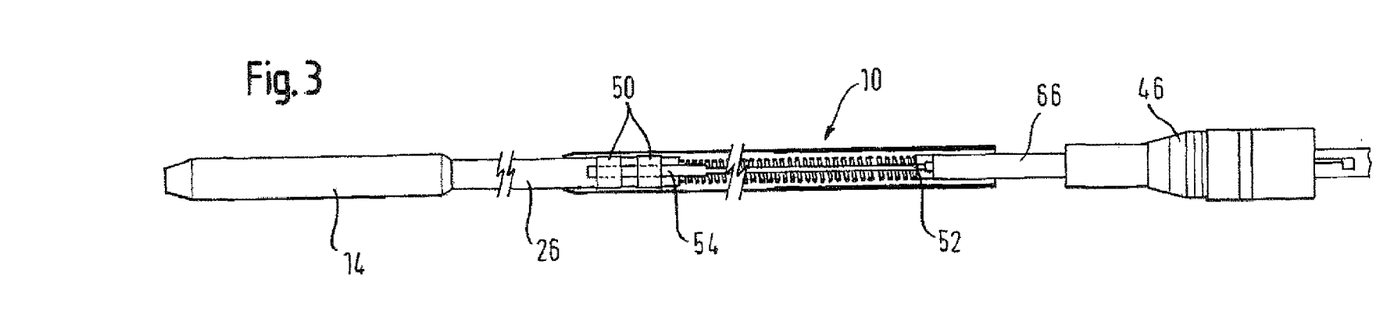
FIG. 3 is a longitudinal diametral section, as in FIGS. 1 and 2, but showing the device in its assembled form.

We briefly turn to FIG. 3 to complete the description of the proximal movement of the distal sheath. FIG. 3 shows a pair of retaining bands 50 that are swaged into rings around a proximal end zone of the diving sheath 26. These rings press onto the outer cylindrical surface of the diving sheath 26, the distal end of a pull wire 52 which has a flattened portion 54 at its distal end that lies underneath the swaged bands 50, pressed against the surface of the diving sheath 26. Laser welding is used, to weld the pull wire to the retaining bands 50. It is tension in the pull wire 52, imposed from proximal of the proximal end 56 of the pull wire 52, that pulls the diving sheath, and hence the distal sheath 14, away from the stent 12.

Reverting to FIG. 2 of the drawings, we see again the stent support tube 18, connection tube 22 and compound catheter portion 24. We also see the proximal end 60 of the tube 28 of the compound catheter portion 24 being held within a transfer ring 62 that is swaged around the proximal end 60.

That transfer ring is welded to a catheter shaft tube 64 of PHYNOX alloy that defines a lumen that channels the pull wire 52.

A proximal sheath 66 surrounds the catheter tube 64, nested, but with the catheter tube 64 away from the rotational axis of the proximal sheath 66. That leaves most of the cross-section of the lumen of the proximal sheath 66 free for flushing liquids and a guidewire. The guidewire lumen defined by the proximal sheath 66 continues into the lumen of the compound catheter portion and stent support tube. The proximal end 68 of the sheath 66 is set in the same hub 46 as carries the proximal end of the casing tube 40, so that there is no relative endwise movement between the casing tube 40 and the proximal sheath 66. Please note that the ratios of diameter to length in FIGS. 2 and 3 of the drawings bears no relation to reality, in which the overall length of the device likely will be substantially more than a 100 cm whereas the passing diameter contemplated is less than 3 mm (7 French or 8 French). It appears from FIG. 2, for example, that the diving sheath 26 will abut the proximal sheath 66, at least when the stent is deployed. However, looking at FIG. 3, we can see a very substantial end-to-end gap between the diving sheath 26 and the distal end of the proximal sheath 66. The representation in FIG. 3 is misleading as to the length of the proximal sheath 66. In practice, it occupies a very substantial portion of the total length of the system. The total length of the distal sheath 14, diving sheath 26 and compound catheter portion 24, proximally as far as the transfer ring 62, will be much less than 50% of the total length of the catheter system. In reality, and prior to deployment of the implant, the proximal end of the diving sheath 26 is a considerable distance away, distally, from the distal end of the proximal sheath 66, as shown in FIG. 3, but contrary to the impression given by the exploded diagram of FIG. 2.

Figure 4:
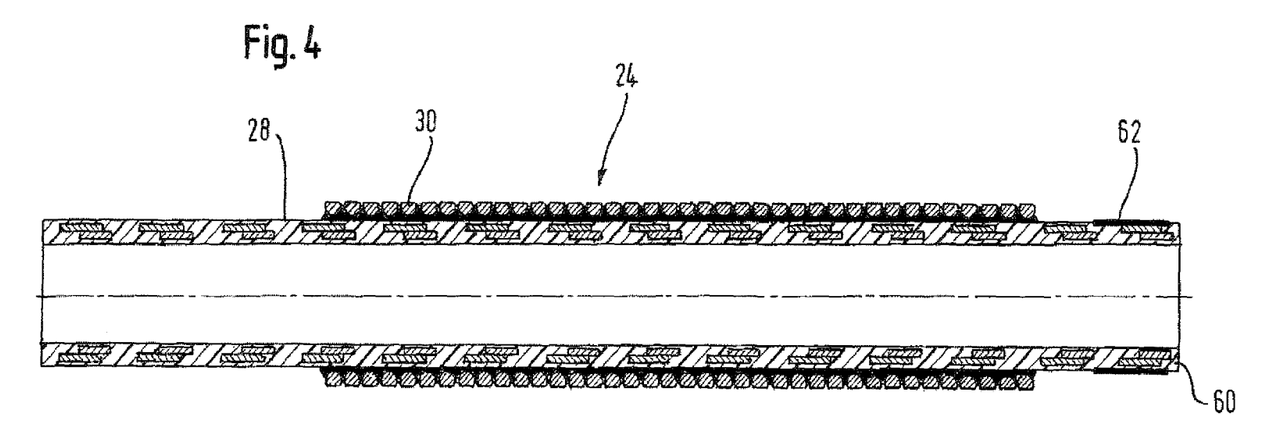
FIG. 4 is a longitudinal diametral section through the compound catheter portion.

For a more detailed description of the compound catheter portion, see the text below, that describes what is shown in FIG. 4 of the drawings.

In operation, the delivery device with its distal end zone looking like it is represented in FIG. 1 is introduced transluminally into the body, and advanced as is known per se, until the distal end is at the location in the body where stenting is desired. At that point, when the stent is to be deployed, the hand unit is actuated, to impose a tensile stress on the pull wire 52, from its proximal end 56. This tensile stress passes through to the distal sheath 14, which moves proximally, with sliding of the diving sheath 26 into the casing tube 40. The stent 12 would be inclined to be carried proximally with the outer sheath 14, except that it is prevented from so doing, by the interaction with the inner surfaces of the covered stent by the cushions 20 of the stent support tube 18. Any tendency of the stent support tube 18 to move proximally with the outer sheath 14 is resisted by compression stress that is generated all the way from the actuation unit along the catheter tube 64, through the transfer ring 62 and along the compound catheter portion 24, up to the end-to-end abutment with the stent support tube 18 inside the connection ring 22, and thence to the cushions 20 and the stent.

After successful deployment of the stent, retraction and removal of the delivery device is relatively straightforward. The cylindrically outside surfaces of the catheter system are generally smooth, and likely anyway to be coated with a lubricious coating. The atraumatic distal tip 16 of the system has stretched to pass proximally over the covered stent but is still residually inwardly tapered during withdrawal of the system. Inside the stent, there is no bulky tip structure that has to pass through the lumen of the stent, from beyond the distal end to proximally of the stent lumen. Instead, the only structure that has to slip proximally out of the stent lumen is hat of the stent support tube 18, which represents a minimal tendency to snag on the inside of the stent.

Turning now to FIG. 4 of the drawings, we find the compound catheter portion 24 shown at a larger scale so that its constructional details can be seen more clearly. The portion 24 is based on a polyimide tube 28 that includes within its annular wall thickness a braid of flat wire. The annular wall thickness is 0.075 mm and the outer diameter is 1.16 mm. The inner diameter is 1.01 mm and the flat braiding wire has a rectangular cross-section of thickness 0.013 mm and width of 0.076 mm. The braid is based on SS304W steel material, braided at 100 PPI (crossing points per inch). There are 16 wire bands altogether in the braid.

Turning now to the helical wind of multi-strand wire on the outer cylindrical surface of the polyimide tube 28, this is glued to the tube with cyanocrylate glue and, after wrapping, the outside diameter of the helical coil is 1.5 mm (to a tolerance of 0.02 mm). After mounting on the tube 28, the helical coil is ground to a final outside diameter of 1.4 mm. As is evident from drawing FIG. 4, the helical coil does not cover the entire axial length of the compound catheter component. Proximally, it stops short of the transfer ring 62. Distally, it stops 50 mm short of the distal end of the tube 28, well short of the connection tube 28 and, as can be seen in drawing FIG. 1, well short of the proximal end of the sheath 14 which lies radially outside the covered stent 12.

Variations in the construction of the delivery device shown in the drawings will be evident to those skilled in the art. Materials selection is part of the routine burden of the delivery system designer, as is choice of methods for reliably connecting individual components of the delivery system. A number of individual features of the stent delivery system are known in themselves, but there are multitudes of features routine to use in stent delivery devices that can be mixed and matched to achieve particular requirements of the delivery task to be performed. The number of design considerations to be taken into account is almost infinite. Thus, putting together a synergistic combination of individual components, that permits the delivery of longer covered stents than hitherto, with greater radial stenting force than hitherto, beyond the capability of any delivery system hitherto available, represents a valuable and important contribution to the art.

INDUSTRIAL APPLICABILITY

A catheter delivery device is disclosed, that has a specific architecture capable of delivering through tortuous bodily lumens with a narrow diameter a covered self-expanding stent with a greater length, and higher stenting force, than would hitherto have been possible.

What is claimed is:

1. A catheter delivery device for a self-expanding stent, comprising:
    a distal catheter component carrying the stent;
    a distal sheath disposed over the distal catheter component and the stent in an insertion position, wherein relative movement of the distal sheath with respect to the distal catheter component and the stent releases the stent;
    a compound catheter portion coupled to the distal catheter component, the compound catheter portion having a stiffness greater than a stiffness of the distal catheter component;

a proximal catheter component having a proximal end attached to a hub and a distal end coupled to the compound catheter portion, wherein:

the proximal catheter component, the compound catheter portion, and the distal catheter component together define a contiguous guidewire lumen from a proximal end of the device to a distal end of the device, and the proximal catheter component surrounds a tube and a pull wire within a lumen of the tube, the pull wire operably connected to the distal sheath via a diving sheath; and a casing tube surrounding the proximal catheter component, the casing tube telescopically receiving the diving sheath upon proximal movement of the pull wire.

2. The catheter delivery device according to claim 1, wherein the casing tube includes a proximal end fixed to the hub.

3. The catheter delivery device according to claim 1, further comprising a ring that retains the pull wire on the diving sheath.

4. The catheter delivery device according to claim 1, wherein a distal end of the pull wire is flattened and pressed against an outer surface of the diving sheath.

5. The catheter delivery device according to claim 4, further comprising a pair of retaining bands positioned around the flattened distal end of the pull wire and the diving sheath, the pair of retaining bands laser welded to the pull wire.

6. The catheter delivery device according to claim 1, wherein the distal sheath includes a distal end tapering radially inwardly to provide an atraumatic tip of the catheter delivery device.

7. The catheter delivery device according to claim 1, wherein the compound catheter portion has a lumen diameter equivalent to a lumen diameter of the distal catheter component.

8. The catheter delivery device according to claim 7, wherein the compound catheter portion is coupled to the distal catheter component via a polyamide connection tube.

9. The catheter delivery device according to claim 7, wherein the compound catheter portion comprises a braid reinforcement in an annular wall.

10. The catheter delivery device according to claim 9, wherein the braid reinforcement includes a helix of flat wire braided at 100 crossing points per inch.

11. The catheter delivery device according to claim 10, wherein the braid reinforcement comprises 16 wire bands having a rectangular shape.

12. The catheter delivery device according to claim 7, wherein the compound catheter portion includes a section within the diving sheath having a helical wind of wire on an outer surface thereof.

13. The catheter delivery device according to claim 1, wherein the distal catheter component includes embossing on an outer surface, the embossing engaging with a luminal surface of the self-expanding stent in the insertion position.

14. The catheter delivery device according to claim 1, wherein the distal catheter component comprises a length portion including a multitude of slits with a length direction of the multitude of slits transverse to the length of the distal catheter component, the length portion with the multitude of slits increasing the flexibility in bending of a proximal end zone of the distal catheter component.

15. The catheter delivery device according to claim 14, wherein the length portion with the multitude of slits extends to a proximal end of the self-expanding stent.

* * * * *

UNITED STATES PATENT AND TRADEMARK OFFICE
CERTIFICATE OF CORRECTION

PATENT NO.        : 11,109,990 B2
APPLICATION NO.   : 15/659496
DATED             : September 7, 2021
INVENTOR(S)       : Juergen Dorn It is certified that error appears in the above-identified patent and that said Letters Patent is hereby corrected as shown below:

In the Claims

Claim 1, Column 8, Line 58, please insert --self-expanding-- before "stent;
Claim 1, Column 8, Line 60, please insert --self-expanding-- before "stent";
Claim 1, Column 8, Line 62, please insert --self-expanding stent and the distal-- before "distal catheter component" and delete "and the stent" immediately thereafter;
Claim 1, Column 8, Line 63, please insert --self-expanding-- before "stent";
Claim 1, Column 9, Line 7, please insert --catheter delivery-- before "device"; and
Claim 1, Column 9, Line 8, please insert --catheter delivery-- before "device.".

Signed and Sealed this
Eleventh Day of July, 2023

Katherine Kelly Vidal
*Director of the United States Patent and Trademark Office*